United States Patent [19]
Koeda et al.

[11] Patent Number: 5,743,848
[45] Date of Patent: Apr. 28, 1998

[54] PORTABLE ENDOSCOPE SYSTEM

[75] Inventors: Takashi Koeda; Hiroshi Sano; Hirohisa Ueda; Kunitoshi Ikeda; Kunikiyo Kaneko; Rensuke Adachi, all of Tokyo, Japan

[73] Assignee: Asahi Kogaku Kogyo Kabushiki Kaisha, Tokyo, Japan

[21] Appl. No.: 701,045

[22] Filed: Aug. 21, 1996

[30] Foreign Application Priority Data

Aug. 31, 1995 [JP] Japan .................. 7-222876
Sep. 6, 1995 [JP] Japan .................. 7-228810

[51] Int. Cl.⁶ .................................. A61B 1/06
[52] U.S. Cl. .............. 600/178; 600/160; 600/199
[58] Field of Search ................... 362/194, 197, 362/186, 196, 804, 208; 600/160, 178, 179, 180, 199, 200, 248–249

[56] References Cited

U.S. PATENT DOCUMENTS

| | | | |
|---|---|---|---|
| 618,057 | 1/1899 | Crowdus | 362/197 |
| 760,395 | 5/1904 | Houghton | 600/200 |
| 3,190,286 | 6/1965 | Stokes | 600/179 X |
| 3,592,199 | 7/1971 | Ostensen | 600/199 X |
| 3,766,909 | 10/1973 | Ozbey | 600/199 |
| 4,580,198 | 4/1986 | Zinnanti, Jr. | 600/178 X |
| 5,097,399 | 3/1992 | Gammache | 362/197 |
| 5,353,208 | 10/1994 | Moore | 362/208 X |
| 5,556,191 | 9/1996 | Maassen | 362/263 X |

*Primary Examiner*—Richard J. Apley
*Assistant Examiner*—John P. Leubecker
*Attorney, Agent, or Firm*—Greenblum & Bernstein, P.L.C.

[57] ABSTRACT

A portable endoscope system has an illuminating light guide for transmitting light for illuminating an object. The light guide has an entrance end portion disposed in an endoscope control part. A light source lamp is contained in an illuminating light supply unit for supplying illuminating light to the light guide. A filament serving as a light emission source in the lamp is disposed such that the longitudinal direction of the filament is approximately perpendicular to an entrance end surface of the light guide. A spheroidal reflecting mirror converges illuminating light emitted from the lamp onto the entrance end surface of the light guide. A bore is provided in a side of the mirror for receiving a head portion of the lamp. A reflecting surface is provided on an inner surface of a rear end portion of the mirror.

10 Claims, 7 Drawing Sheets

PORTABLE ENDOSCOPE SYSTEM

BACKGROUND OF THE INVENTION

The present disclosure relates to subject matter contained in Japanese Patent Application No. 7-222876 (filed on Aug. 31, 1995) and Japanese latent Application No. 7-228810 (filed on Sep. 6, 1995), which are expressly incorporated herein by reference in their entireties.

1. Field of the Invention

The present invention relates to a portable endoscope system in which an illuminating light supply unit, containing an electric lamp for supplying illuminating light to a light guide, is attached to an endoscope control part.

2. Description of the Prior Art

A conventional portable endoscope system has a light-emitting device for illumination which is provided in an endoscope control part. Such a conventional portable endoscope system is generally arranged such that an entrance end portion of a light guide for transmitting light for illuminating an object is disposed in the endoscope control part, and an illuminating light supply unit is attached to the control part. The illuminating light supply unit contains a miniature bulb for supplying illuminating light to the light guide.

Figure 7:
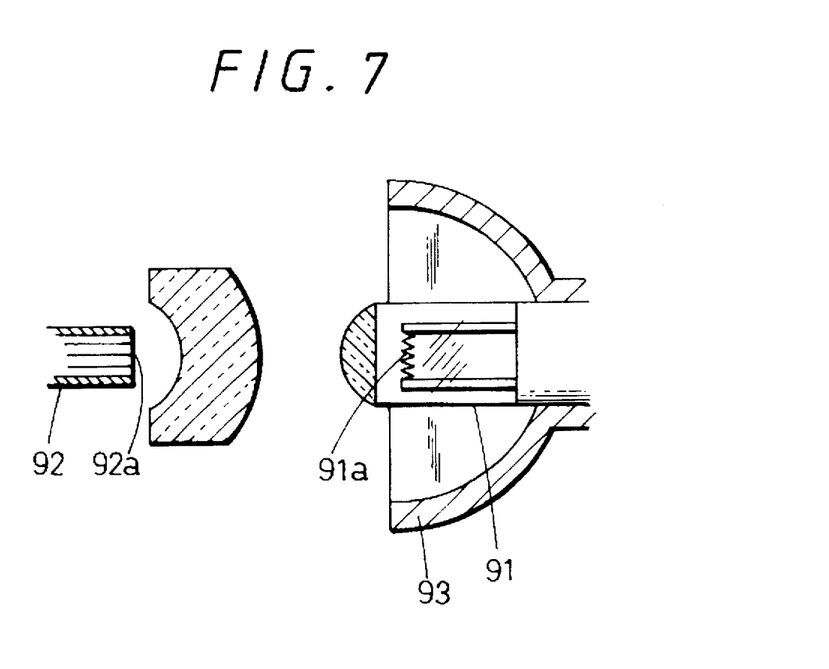
FIG. 7 is a fragmentary sectional side view showing a light source part of a conventional portable endoscope system.

As shown in FIG. 7, a miniature bulb 91 in a conventional portable endoscope system has a filament 91a which is disposed such that the longitudinal direction of the filament 91a is parallel to an entrance end surface 92a of a light guide 92. Light emitted from the filament 91a is reflected by a mirror, e.g., a spheroidal mirror 93, so as to converge on the entrance end surface 92a of the light guide 92.

The above-described conventional arrangement suffers, however, from some problems, as stated below. Because the longitudinal direction of the filament 91a is parallel to the entrance end surface 92a of the light guide 92, the cross-sectional configuration of a convergent bundle of rays (i.e., beam) on the entrance end surface 92a of the light guide 92 is undesirably elongate, and a part of the ray bundle extends off the entrance end surface 92a of the light guide 92. Consequently, a large amount of light is wasted 2nd does not enter the light guide 92. Therefore, it is impossible to illuminate the object brightly.

Furthermore, if the arrangement is such that the miniature bulb 91 is inserted into the spheroidal mirror 93 from the rear end of the mirror 93, the spheroidal mirror 93 cannot have a reflecting surface at the rear end for reflecting illuminating light in the axial direction. Accordingly, there are substantially no light rays entering the light guide 92 at angles close to right angles to the entrance end surface 92a. Consequently, illuminating light that is applied to the object has 2n annular luminous intensity distribution in which the central portion of the observation field is undesirably dark. Therefore, there are cases where favorable observation cannot be performed.

SUMMARY OF THE INVENTION

An object of the present invention is to provide a portable endoscope system capable of brightly illuminating an object by efficiently converging a bundle of light rays emitted from a filament onto an entrance end surface of an illuminating light guide.

Another object of the present invention is to provide a portable endoscope system capable of effecting favorable illumination without a doughnut-shaped luminous intensity distribution in which the central portion of the observation field is undesirably dark.

Other objects and advantages of the present invention will become apparent from the following detailed description of illustrated embodiments of the invention.

According to the present invention, there is provided a portable endoscope system having an illuminating light guide for transmitting light for illuminating an object. The illuminating light guide has an entrance end portion mounted in an endoscope control part. A light source lamp is contained in an illuminating light supply unit for supplying illuminating light to the illuminating light guide. A filament serving as a light emission source in the light source lamp is supported such that the longitudinal direction of the filament is substantially perpendicular to an entrance end surface of the illuminating light guide.

In addition, there is provided a portable endoscope system having an illuminating light guide for transmitting light for illuminating an object. The illuminating light guide has an entrance end portion mounted in an endoscope control part. A light source lamp is contained in an illuminating light supply unit for supplying illuminating light to the illuminating light guide. A spheroidal reflecting mirror converges illuminating light emitted from the light source lamp onto an entrance end surface of the illuminating light guide. The spheroidal reflecting mirror has a bore formed at a side of the spherodical reflecting mirror for passing a head portion of the light source lamp. The spheroidal reflecting mirror has a reflecting surface on the inner surface of a rear end portion thereof.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
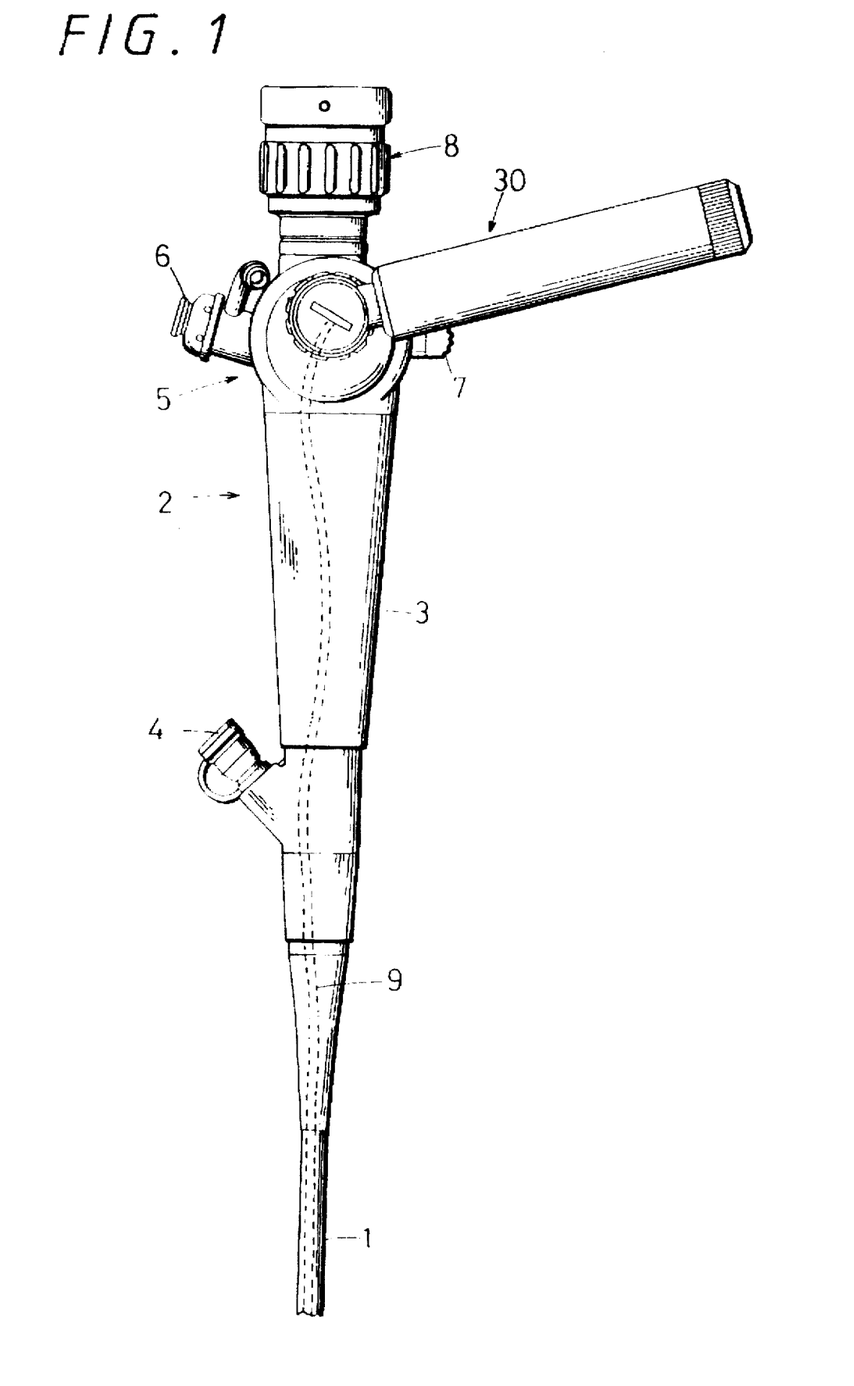
FIG. 1 is a side view showing a first embodiment of the present invention with an illuminating light supply unit attached to an endoscope control part.
Figure 2:
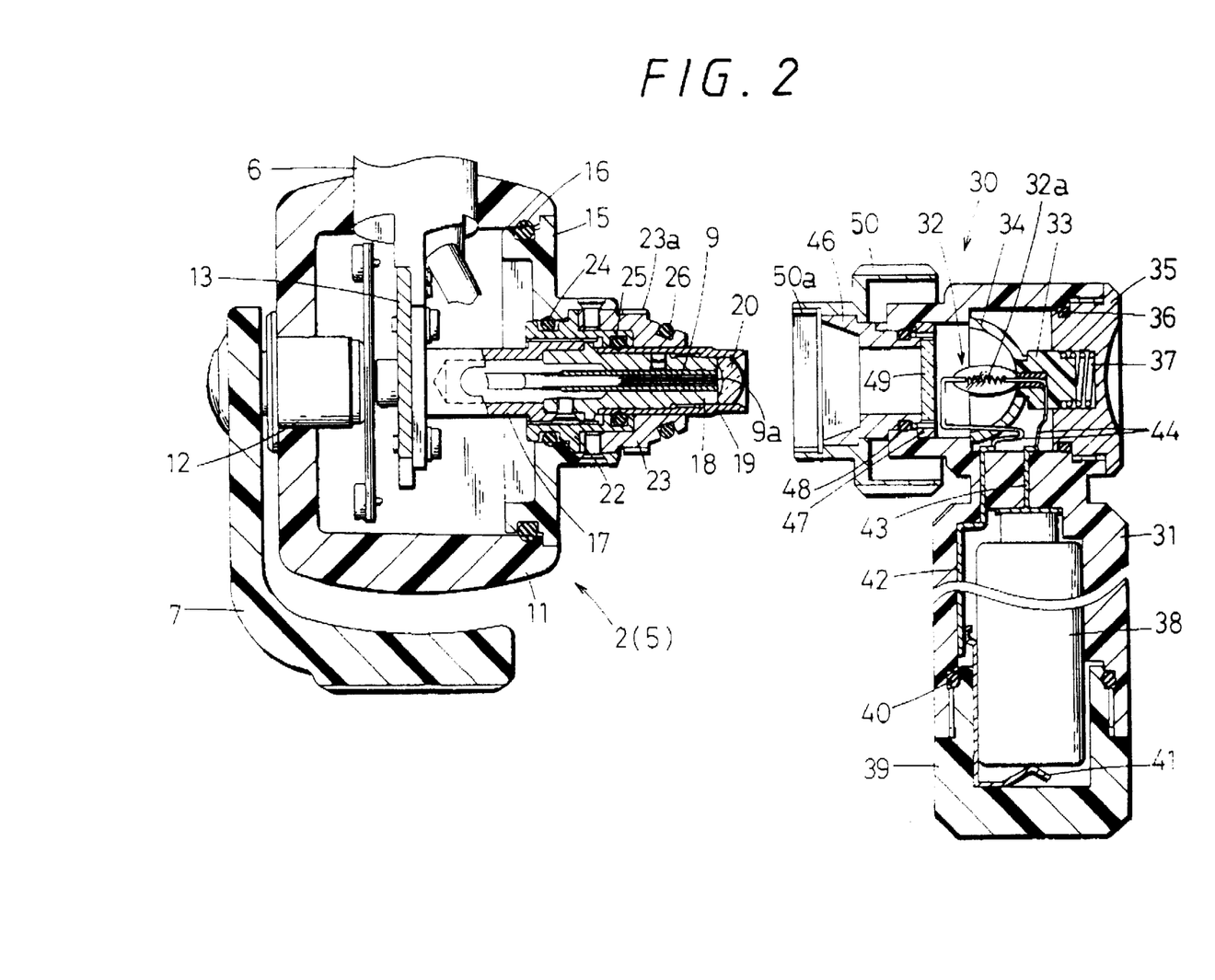
FIG. 2 is a sectional plan view showing the first embodiment of the present invention with the illuminating light supply unit detached from the endoscope control part.
Figure 3:
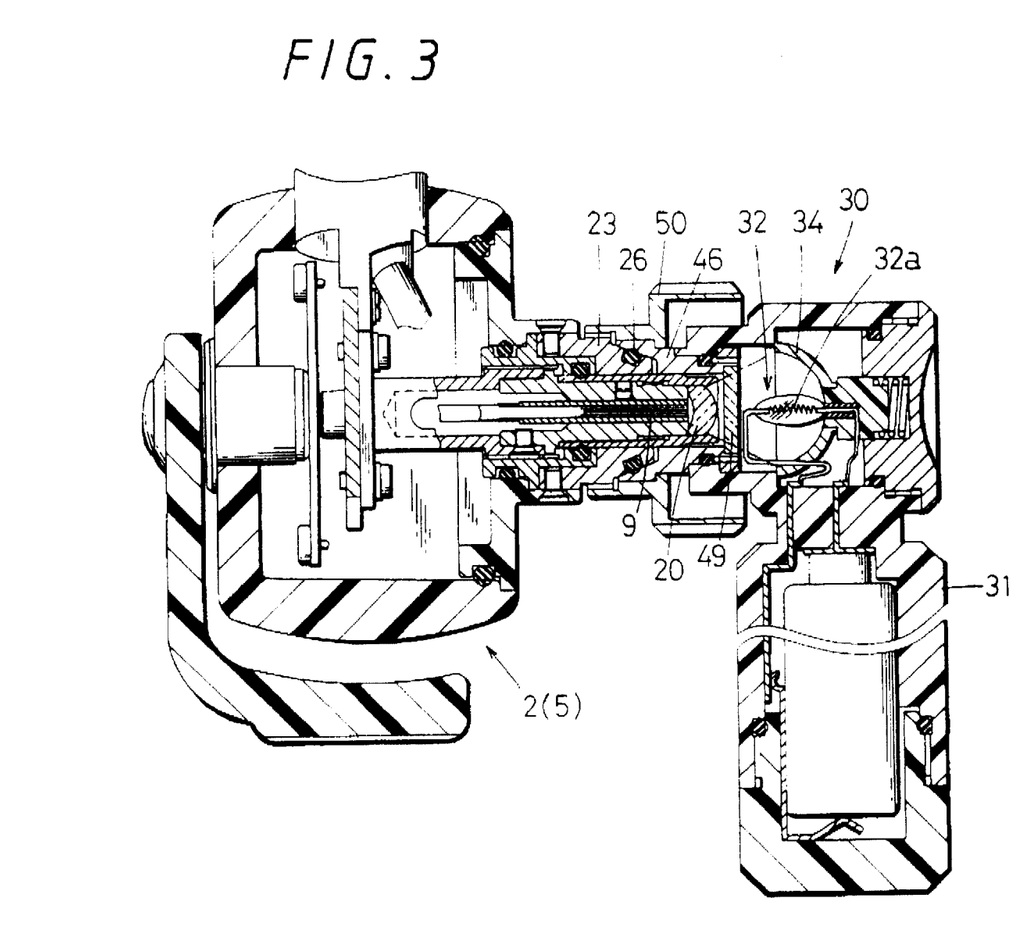
FIG. 3 is a sectional plan view showing the first embodiment of the present invention with the illuminating light supply unit attached to the endoscope control part.

FIGS. 1 to 3 show a first embodiment of the present invention.

Referring to FIG. 1, a portable endoscope system according to the first embodiment of the present invention has an insert part 1 which is armored with a flexible tube, and a control part 2 which is connected to the base end of the insert part 1.

About three fourths from the bottom of the control part 2 is a grip portion 3. A forceps inlet 4 is provided between the grip portion 3 and the insert part 1 so as to project obliquely forward.

The control part 2 has a control mechanism portion 5 above the grip portion 3. The control mechanism portion 5 has a suction control valve 6 which is disposed on the front side thereof to carry out a suction operation through a forceps channel (not shown) inserted in the insert part 1. The control mechanism portion 5 further has a bending control lever 7 which is disposed on the rear side thereof to effect bending control of a remote-controlled bendable portion (not shown) which is formed at the distal end of the insert part 1. In addition, an eyepiece 8 is provided on the top of the control mechanism portion 5.

A light guide fiber bundle 9 for transmitting light for illuminating an object has an entrance end portion thereof disposed in the control mechanism portion 5, and extends through the insert part 1 and the grip portion 3 of the control part 2. The exit end portion of the light guide fiber bundle 9 is disposed in the distal end of the insert part 1.

An illuminating light supply unit 30 for supplying illuminating light to the light guide fiber bundle 9 is detachably attached to a side of the control mechanisim portion 5.

FIG. 2 is an enlarged sectional view showing the portable endoscope system in a state where the illuminating light supply unit 30 is detached from the control part 2.

The control mechanism portion 5 of the control part 2 is armored with a casing 11 made of a plastic material. A lever bearing cylinder 12 that supports the bending control lever 7 is fitted in a through-hole provided in the casing 11, and sealed in a watertight mariner. Similarly, the suction control valve 6 is fitted in a through-hole provided in the casing 11, and sealed in a watertight manner. The respective base end portions of the lever bearing cylinder 12 and the suction control valve 6 are secured to a frame 13 in the control part 2.

A cover 15 is fitted in a relatively large opening provided in a side of the casing 11, and a sealing O-ring 16 is attached to the fitting surface of the cover 15 to prevent water from entering the inside of the control part 2 through the gap between the cover 15 and the peripheral wall of the opening. It should be noted that, although the O-ring 16 is compressed when it is held between the cover 15 and the casing 11, the cross-sectional configuration of the O-ring 16 in a natural state before it is compressed is shown in the figure (the same shall apply hereinafter).

A support cylinder 17 is disposed on the central axis of a bore formed in the center of the cover 15. The base end portion of the support cylinder 17 is secured to the frame 13 in the control part 2. A light guide mounting cylinder 18 is screwed to the support cylinder 17. The distal end portion of the light guide mounting cylinder 18 projects outwardly from the support cylinder 17. The entrance end portion of the light guide fiber bundle 9 is secured with a screw at the central axis position in the light guide mounting cylinder 18.

A lens mounting cylinder 19 is fitted on the projecting end portion of the light guide mounting cylinder 18 in a cap-like fashion, and firmly thread-engaged with it. The lens mounting cylinder 19 has a convex meniscus lens 20 which is bonded to the distal end portion thereof in a watertight mariner. Thus, the convex meniscus lens 20 is set at a position close to the entrance end surface 9a of the light guide fiber bundle 9 so as to face it.

An O-ring retaining frame 22 is disposed to surround the joint between the support cylinder 17 and the light guide mounting cylinder 18. The O-ring retaining frame 22 is fitted at the outer surface of the frame 22 to the wall of the bore provided in the center of the cover 15, and fitted at the inner surface of the frame 22 to the outer surface of the lens mounting cylinder 19. O-rings 24 and 25 are attached to the outer and inner surfaces, respectively, of the O-ring retaining frame 22 to prevent water from entering the inside of the control part 2 through the gap between the O-ring retaining frame 22 and the cover 15 or through the gap between the O-ring retaining frame 22 and the lens mounting cylinder 19.

A connecting cylinder 23 is disposed to surround an area which extends from the lens mounting cylinder 19 to the O-ring retaining frame 22. The base end portion of the connecting cylinder 23 is screwed to the inner surface of the bore in the cover 15. The outer peripheral surface of an intermediate portion of the connecting cylinder 23 is provided with an external thread 23a. The outer peripheral surface of the distal end portion of the connecting cylinder 23, which lies forward of the external thread 23a, is a tapered surface which becomes gradually smaller in diameter toward the distal end. A scaling O-ring 26 is attached to the tapered surface at an intermediate position between the external thread 23a and the distal end.

The illuminating light supply unit 30 has an L-shaped cylindrical configuration as a whole. The illuminating light supply unit 30 has a casing 31 made of a plastic material. A light source lamp 32, which is a miniature bulb, is disposed in the bend of the L-shaped casing 31. The light source lamp 32 is attached to a lamp socket 33.

The light source lamp 32 has an elongate configuration. The light source lamp 32 is supported such that the longitudinal direction of the lamp 32 extends toward the light guide fiber bundle 9. The light source lamp 32 has a filament 32a as a light emission source. The filament 32a is supported such that the longitudinal direction of the filament 32a is coincident with the longitudinal axis of the light source lamp 32. The filament 32a emits light by being supplied with an electric current.

Accordingly, the longitudinal direction of the filament 32a is coincident with the longitudinal direction of the fibers in the entrance end portion of the light guide fiber bundle 9. Thus, the longitudinal direction of the filament 32a is substantially perpendicular to the entrance end surface 9a of the light guide fiber bundle 9.

The light source lamp 32 is positioned on the axis of the short cylindrical portion of the L-shaped casing 31, which is connected to the control part 2. A spheroidal reflecting mirror 34 is attached to the lamp socket 33 so as to surround the light source lamp 32 in order to converge illuminating light from the light source lamp 32 onto the axis of the short cylindrical portion of the L-shaped casing 31.

The filament 32a of the Light source lamp 32 is supported such that the longitudinal direction of the filament 32a lies on the axis of the spheroidal reflecting mirror 34, and that the central portion of the filament 32a lies at the focal point of the spheroidal reflecting mirror 34.

The casing 31 is formed with an opening behind the lamp socket 33. A bottom cover 35 is detachably thread-engaged with the mouth of the opening. A sealing O-ring 36 is disposed between the fitting surfaces of the bottom cover 35 and the casing 31 to prevent water from entering the inside of the illuminating light supply unit 30 through the gap between the bottom cover 35 and the casing 31. In addition, a helical compression spring 37 is interposed between the bottom cover 35 and the lamp socket 33 to secure the lamp socket 33 and the spheroidal reflecting mirror 34 by resilient force from the spring 37.

A battery 38 is accommodated in the long cylindrical portion of the L-shaped casing 31. The battery 38 may be either a dry battery or a rechargeable nickel-cadmium battery.

A battery casing cover 39 made of a plastic material is detachably thread-engaged with an opening provided at an outer end of the battery accommodating portion of the casing 31. A sealing O-ring 40 is disposed in the boundary between the battery casing cover 39 and the peripheral wall of the opening to prevent water from entering the inside of the illuminating light supply unit 30 through the gap therebetween. The battery 38 can be replaced by detaching the battery casing cover 39 from the casing 31.

Negative electrodes 41 and 42 are disposed in the battery casing cover 39 and the casing 31, respectively. A positive electrode 43 is disposed in the casing 31. The electrodes 42 and 43 are connected to the light source lamp 32 through respective lead wires 44.

It should be noted that a switch (not shown) for ON/OFF controlling the light source lamp 32 is provided in an intermediate portion of the wiring for supplying electric power to the light source lamp 32. The switch is also sealed in a watertight manner so that water cannot externally enter the inside of the illuminating light supply unit 30.

A connecting cylinder receiving cylinder 46 is secured in an opening provided at the end of the short cylindrical portion of the L-shaped casing 31 by fastening a nut 47 from the inner side of the casing 31. The connecting cylinder receiving cylinder 46 has a tapered opening which is so shaped as to engage with the tapered surface of the connecting cylinder 23, which is provided on the control part 2.

A sealing O-ring 48 is disposed between the fitting surfaces of the connecting cylinder receiving cylinder 46 and the casing 31 to prevent water from entering the inside of the illuminating light supply unit 30 through the gap therebetween. A plane-parallel transparent plate 49 is bonded to the inner end portion of the connecting cylinder receiving cylinder 46 in a watertight manner.

Further, a fastening ring 50 is attached to the outer peripheral portion of the connecting cylinder receiving cylinder 46 to axially engage to the connecting cylinder 23. The fastening ring 50 has an internal thread 50a for engagement with the external thread 23a of the connecting cylinder 23.

Accordingly, when the illuminating light supply unit 30 which is in the state shown in FIG. 2 is to be connected to the control part 2, the illuminating light supply unit 39 is brought close to the control part 2, and the tapered surfaces of the connecting cylinder 23 and the connecting cylinder receiving cylinder 46 are brought into close contact with each other. Then, the internal thread 50a of the fastening ring 50 is engaged with the external thread 23a of the connecting cylinder 23. Thus, the illuminating light supply unit 30 is connected to the control part 2, as shown in FIG. 3.

In the portable endoscope system having the illuminating light supply unit 30 attached to the control part 2 as described above, a bundle of light rays emitted from the filament 32a of the light source lamp 32 is reflected by the spheroidal reflecting mirror 34, and then passes through the transparent plate 49 and the convex meniscus lens 20. Thus, the ray bundle converges on the entrance end surface 9a of the light guide fiber bundle 9, and enters the light guide fiber bundle 9.

At this time, because the filament 32a is positioned such that its longitudinal direction is approximately perpendicular to the entrance end surface 9a of the light guide fiber bundle 9, the cross-sectional configuration of the convergent ray bundle on the entrance end surface 9a is not elongate as in the prior art. Accordingly, substantially no part of the ray bundle extends off the entrance end surface 9a, and almost all the light rays enter the light guide fiber bundle 9 without waste.

As a result, the bundle of light rays emitted from the filament 32a of the light source lamp 32 enters the light guide fiber bundle 9 with a minimal loss and is efficiently applied to the object. Thus, the object can be brightly illuminated.

According to the first embodiment of the present invention, the filament of an electric lamp that emits illuminating light is supported such that the longitudinal direction of the filament is approximately perpendicular to the entrance end surface of the illuminating light, guide. Therefore, a bundle of light rays emitted from the filament can be made to enter the illuminating light guide efficiently without any part thereof extending off the entrance end surface of the illuminating light guide. Thus, the object can be brightly illuminated.

Figure 4:
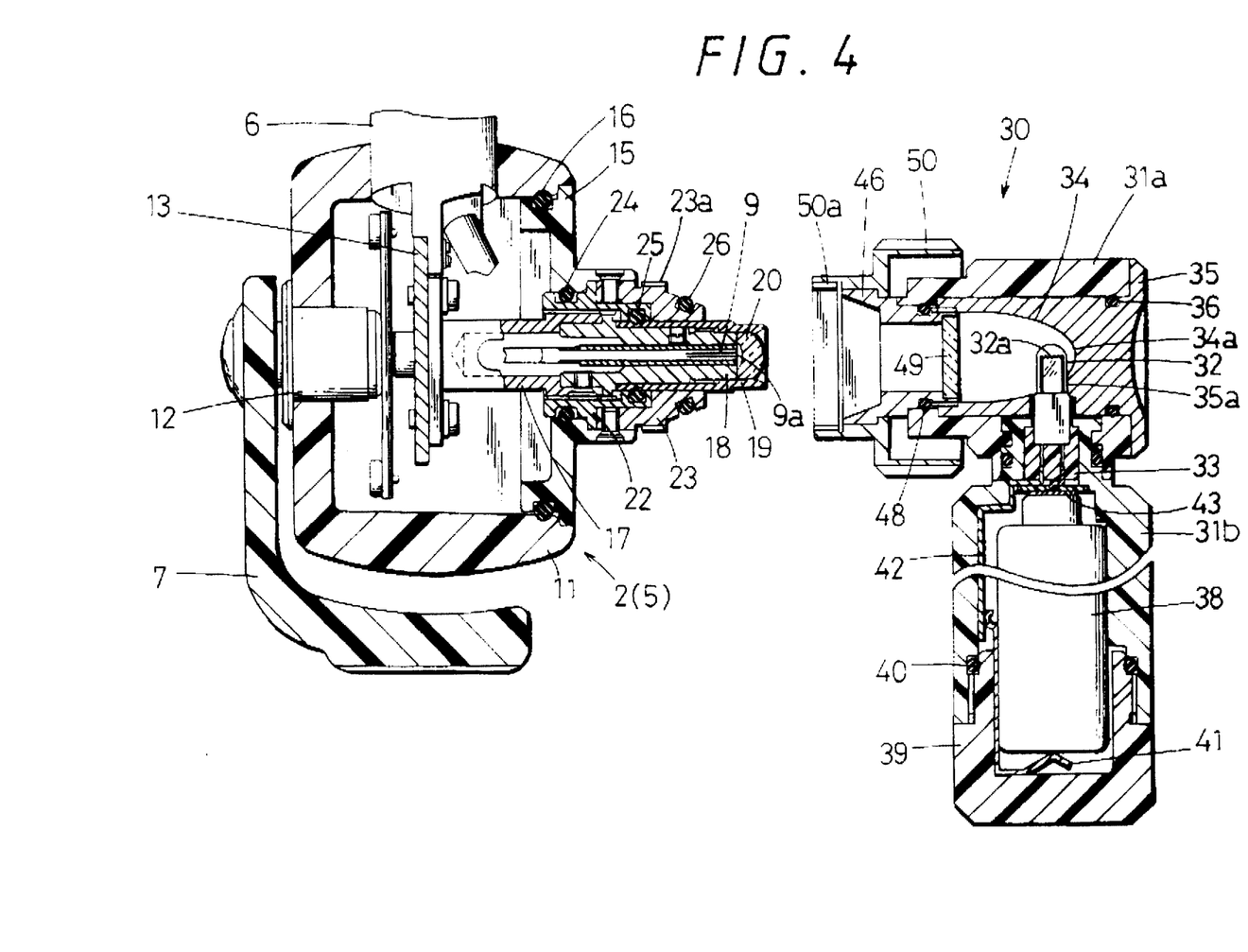
FIG. 4 is a sectional plan view showing a second embodiment of the present invention with an illuminating light supply unit detached from an endoscope control part.
Figure 5:
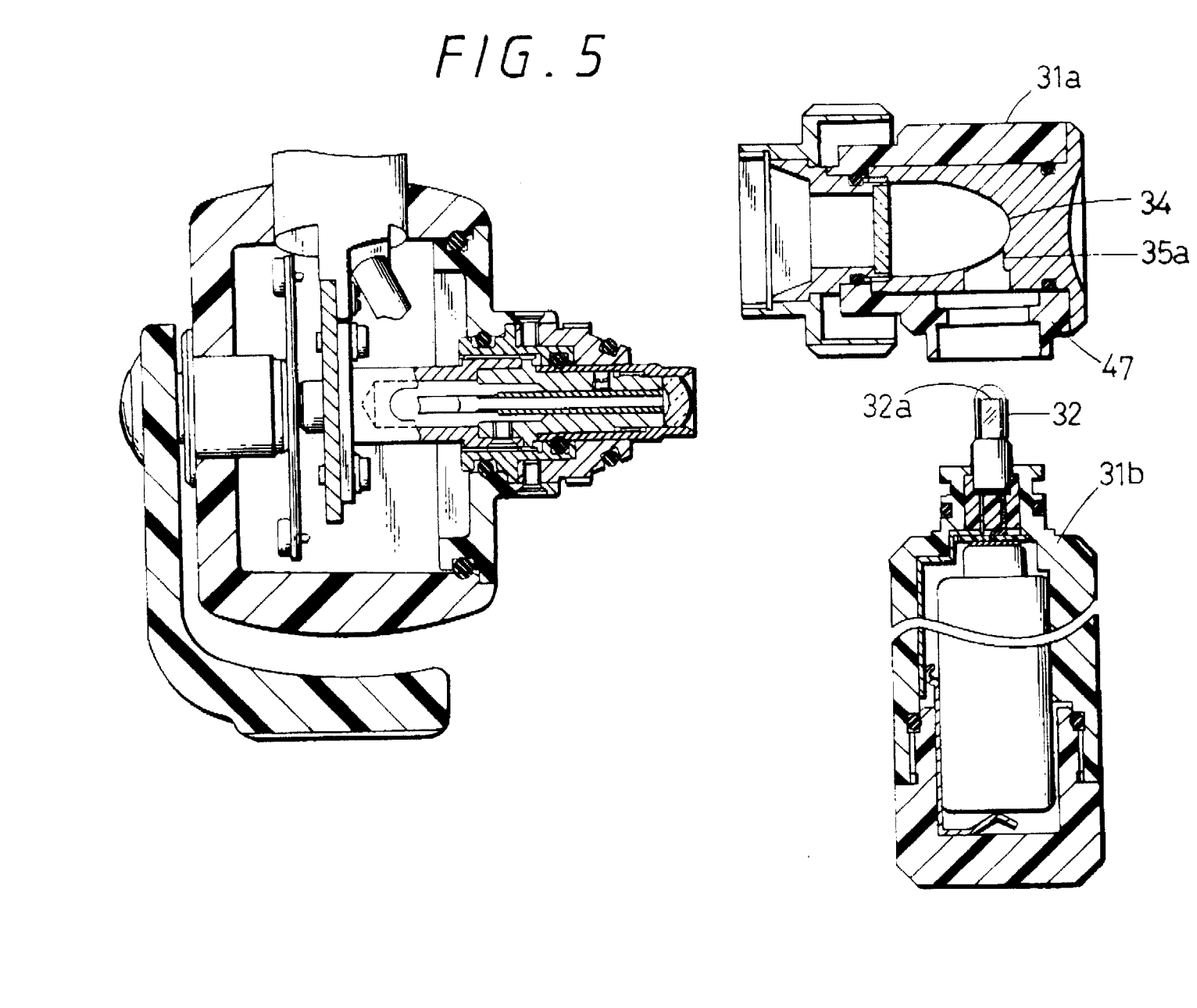
FIG. 5 is a sectional plan view showing the second embodiment of the present invention in a state where a lamp chamber and a battery chamber are detached from each other.
Figure 6:
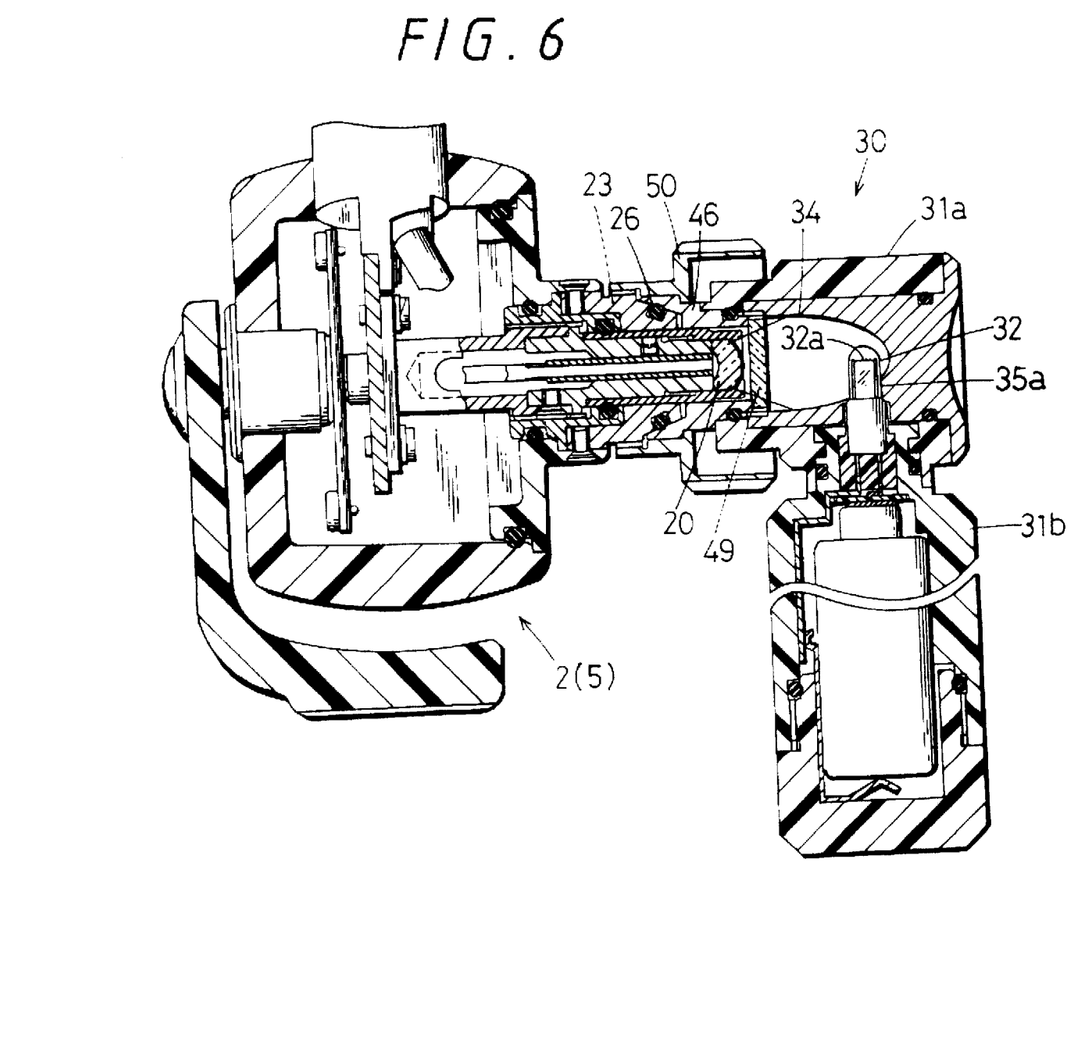
FIG. 6 is a sectional plan view showing the second embodiment of the present invention with the illuminating light supply unit attached to the endoscope control part.

FIGS. 4 to 6 show a second embodiment of the present invention. The second embodiment differs from the first embodiment only in the arrangement of the illuminating light supply unit 30, containing the light source lamp 32 and the spheroidal reflecting mirror 34.

FIG. 4 is a sectional plan view showing the second embodiment of the present invention with the illuminating light supply unit 30 detached from the control part 2.

In this embodiment, the casing 31 is divided into a lamp chamber casing 31a and a battery chamber casing 31b. The two casings 31a and 31b are detachably connected together such that their axes are perpendicular to each other.

The lamp chamber casing 31a has a lamp chamber plug member 35 fitted thereinto from the rear end of the casing 31a with a sealing O-ring 36 interposed therebetween. The lamp chamber plug member 35 has a spheroidal reflecting mirror 34 formed thereon such that the axis of the mirror 34 extends toward the entrance end surface 9a of the light guide fiber bundle 9, coinciding with the axis of the light guide fiber bundle 9.

A light source lamp 32, which is a miniature bulb, has electrodes extending from its base end portion. The electrodes are inserted straight into a lamp socket 33 which is disposed in a connection end portion of the battery chamber casing 31b, thereby securing the light source lamp 32 to the lamp socket 33. The head portion of the light source lamp 32 is removably inserted into the inside of the spheroidal reflecting mirror 34 through a bore 35a provided in a side of the lamp chamber plug member 35.

The light source lamp 32 has a filament 32a sealed therein, close to the distal end of the lamp 32. The filament 32a is supported such that the longitudinal direction of the filament 32a is perpendicular to the axis of the light source lamp 32. The filament 32a lies on the axis of the spheroidal reflecting mirror 34, and the center position of the filament 32a is approximately coincident with the focus position of the spheroidal reflecting mirror 34. Since center position of the filament 32a is approximately coincident with the focus position of the spheroidal reflecting mirror 34, the aforementioned axis of the spheroidal reflecting mirror 34 is necessarily the optical axis of the spheroidal reflecting mirror 34. In order to place the filament 32a in this position, the bore 35a is formed in the lamp chamber member at a side position relative to the focus position of the spheroidal reflecting mirror 34.

Accordingly, the reflecting surface of the spheroidal reflecting mirror 34 is ineffective only at the side portion corresponding to the bore 35a (in which the light source lamp 32 is inserted). That is, the reflecting surface has no ineffective portion on the inner surface of the rear end portion 34a is close to the axis.

FIG. 5 shows the second embodiment in a state where the lamp chamber casing 31a and the battery chamber casing 31b are detached from each other. As shown in the figure, the light source lamp 32 projects from the head portion of the battery chamber casing 31b.

Accordingly, the light source lamp 32 is set in the above-described position by connecting the battery chamber casing 31b to the lamp chamber casing 31a. It is possible to use any type of mechanism for connecting the lamp chamber casing 31a and the battery chamber casing 31b. For example, thread engagement, a bayonet base-socket mechanism, or a click mechanism may be used.

Referring to FIG. 4, a battery 38 is accommodated in the battery chamber casing 31b. The battery 38 may be either a dry battery or a rechargeable nickel-cadmium battery.

A connecting cylinder receiving cylinder 46 is connected to the lamp chamber filling member 35 by thread engagement. The connecting cylinder receiving cylinder 46 has a tapered opening which is so shaped as to engage with the tapered surface of the connecting cylinder 23, which is provided on the control part 2.

The other portions of the second embodiment are the same as those of the first embodiment. Therefore, the same portions are denoted by the same reference characters as those in the first embodiment, and detailed description thereof is omitted.

Thus, similarly to the first embodiment in the second embodiment when the illuminating light supply unit 30 is attached to the control part 2 as shown in FIG. 6, a bundle of light rays emitted from the filament 32a of the light source lamp 32 is reflected by the spheroidal reflecting mirror 34, and then passes through the transparent plate 49 and the convex meniscus lens 20. Thus, the ray bundle converges (without an elongate shape) on the entrance end surface 9a of the light guide fiber bundle 9, and enters the light guide fiber bundle 9.

At this time, light rays close to the axis of the entrance end portion of the light guide fiber bundle 9 also efficiently enter the light guide fiber bundle 9 because there is a reflecting surface on the inner surface of the rear end portion 34a of the spheroidal reflecting mirror 34, and the base end portion of the light source lamp 32 lies at a side of the spheroidal reflecting mirror 34 and therefore does not intercept reflected light. Accordingly, illumination for an object can be effected without an annular luminous intensity distribution in which the central portion of the observation field is undesirably dark. Thus, it is possible to obtain a favorable image for observation.

It should be noted that, the spheroidal reflecting mirror 34 is provided in a side thereof with the bore 35a for inserting the light source lamp 32, and illuminating light is not reflected at that portion of the mirror 34. However, the area occupied by the bore 35a is only a very small part of the entire peripheral surface (reflecting surface) of the spheroidal reflecting mirror 34. Therefore, the bore 35a has a minimal effect on the illumination uniformity.

According to the second embodiment of the present invention, a light source lamp is secured by inserting the head portion of the lamp into the inside of a spheroidal reflecting mirror through a bore provided in a side of the mirror, and a reflecting surface is provided on the inner surface of the rear end portion of the spheroidal reflecting mirror. Therefore, light rays close to the axis of the entrance end portion of the illuminating light guide efficiently enter the light guide.

Accordingly, illumination for an object can be effected without an annular luminous intensity distribution in which the central portion of the observation field is undesirably dark. Thus, it is possible to obtain a favorable image for observation.

While the invention has been described by reference to specific embodiments chosen for purposes of illustration, it should be apparent that numerous modifications could be made thereto by those skilled in the art without departing from the basic concept and scope of the invention.

We claim:

1. A portable endoscope system comprising an endoscope control part that controls bending of an insert part;

an illuminating light guide extending through said insert part for transmitting light for illuminating an object, said illuminating light guide having an entrance end portion disposed in said endoscope control part;

an illuminating light supply unit attached to said endoscope control part and being detachable with respect to said endoscope control part;

a light source lamps contained in said illuminating light supply unit, for supplying illuminating light to said illuminating light guide a filament serving as a light emission source in said light source lamp, said filament being supported such that a longitudinal direction of said filament is substantially perpendicular to an entrance end surface of said illuminating light guide; and a spheroidal reflecting mirror, contained in said illuminating light supply unit, said spheroidal reflecting mirror converging light emitted from said filament to said entrance end surface of said illuminating light guide.

2. A portable endoscope system according to claim 1, wherein said filament is supported such that the longitudinal direction of said filament is coincident with a longitudinal direction of said light source lamp.

3. A portable endoscope system according to claim, 1 wherein said filament is supported at a focus position of said spheroidal reflecting mirror.

4. A portable endoscope system according to claim 3, wherein said filament is supported such that the longitudinal direction of said filament is coincident with an optical axis of said spheroidal reflecting mirror.

5. A portable endoscope system according to claim 4, further comprising a convex meniscus lens for allowing illuminating light reflected by said spheroidal reflecting mirror to enter the entrance end surface of said illuminating light guide, said convex meniscus lens being disposed between said spheroidal reflecting mirror and the entrance end surface of said illuminating light guide.

6. A portable endoscope system comprising;

an endoscope control part that controls bending of an insert part;

an illuminating light guide extending through said insert part for transmitting light for illuminating an object, said illuminating light guide having an entrance end portion disposed in said endoscope control part;

an illuminating light supply unit attached to said endoscope control part and being detachable with respect to said endoscope control part;

a light source lamp contained in said illuminating light supply unit, for supplying illuminating light to said illuminating light guide a spheroidal reflecting mirror, contained in said illuminating light supply unit, for converging illuminating light emitted from said light source lamp onto an entrance end surface of said illuminating light guide, said spheroidal reflecting mirror having a bore formed in a side of said spherical reflecting mirror for receiving a head portion of said light source lamp, said spheroidal reflecting mirror having a reflecting surface on an inner surface of a rear end portion of said spheroidal reflecting mirror.

7. A portable endoscope system according to claim 6, wherein said light source has a filament as a light-emitting part, said filaments being supported at a focus position of said spheroidal reflecting mirror.

8. A portable endoscope system according to claim 7, wherein said filament is supported such that a longitudinal direction of said filament is coincident with an optical axis of said spheroidal reflecting mirror.

9. A portable endoscope system according to claim 7, wherein said light source lamp is externally and removably inserted into said bore provided in said side of said spheroidal reflecting mirror.

10. A portable endoscope system according to claim 9, wherein a power supply for lighting said light source lamp is detachable from said spheroidal reflecting mirror.

* * * * *

UNITED STATES PATENT AND TRADEMARK OFFICE
CERTIFICATE OF CORRECTION

PATENT NO. : 5,743,848
DATED : April 28, 1998
INVENTOR(S) : T. KOEDA et al.

It is certified that error appears in the above-identified patent and that said Letters Patent is hereby corrected as shown below:

At column 8, line 17 (claim 1, line 1), change "comprising an endoscope" to ---comprising:---.

At column 8, line 18, (claim 1, line 2), change "control part" to ---an endoscope control part---.

At column 8, line 27 (claim 1, line 10), change "lamps" to ---lamp,---.

At column 8, line 29 (claim 1, line 12), after "guide" insert ---;---.

At column 8, line 59 (claim 6, line 3), change "part:" to ---part;---.

Signed and Sealed this

Twenty-second Day of September, 1998

*Attest:*

BRUCE LEHMAN

*Attesting Officer*    Commissioner of Patents and Trademarks